US00PP22129P2

(12) United States Plant Patent
Probst

(10) Patent No.: US PP22,129 P2
(45) Date of Patent: Sep. 6, 2011

(54) ***COREOPSIS* PLANT NAMED 'SALSA'**

(50) Latin Name: *Coreopsis hybrid*
Varietal Denomination: Salsa

(76) Inventor: Darrell R. Probst, Hubbardston, MA (US)

( * ) Notice: Subject to any disclaimer, the term of this patent is extended or adjusted under 35 U.S.C. 154(b) by 0 days.

(21) Appl. No.: 12/660,464

(22) Filed: Feb. 26, 2010

(51) Int. Cl.
*A01H 5/00* (2006.01)

(52) U.S. Cl. ..... Plt./417

(58) Field of Classification Search ..... Plt./417
See application file for complete search history.

*Primary Examiner* — June Hwu
(74) *Attorney, Agent, or Firm* — Penny J. Aguirre

(57) ABSTRACT

A new cultivar of hybrid *Coreopsis* named 'Salsa' characterized by its inflorescences with ray florets that are gold in color with a large dark red eye zone, its bushy and relatively short plant habit, its floriferous and long blooming habit, its relative sterility, and its vigorous growth habit.

2 Drawing Sheets

Botanical classification: *Coreopsis* hybrid.
Variety denomination: 'Salsa'.

CROSS REFERENCE TO A RELATED APPLICATION

This application is co-pending with a U.S. Plant Patent application filed for a plant derived from similar parentage in the Inventor's breeding program that is entitled *Coreopsis* Plant Named 'Caliente' (U.S. Plant Pat. No. 21,869), *Coreopsis* Plant Named 'Limbo' (U.S. Plant patent application Ser. No. 12/660,455), *Coreopsis* Plant Named 'Cha Cha Cha' (U.S. Plant patent application Ser. No. 12/660,480), *Coreopsis* Plant Named 'Mambo' (U.S. Plant patent application Ser. No. 12/660,454), *Coreopsis* Plant Named 'Jive' (U.S. Plant patent application Ser. No. 12/660,491).

BACKGROUND OF THE INVENTION

The present invention relates to a new and distinct cultivar of *Coreopsis* plant, botanically of hybrid origin and known as *Coreopsis* 'Salsa' and will be referred to hereinafter by its cultivar name, 'Salsa'. The new cultivar of *Coreopsis* is an herbaceous annual grown for use in borders and containers.

The new invention arose from an ongoing controlled breeding program in Hubbardston, Mass. The objective of the breeding program is to develop hybrid cultivars of *Coreopsis* with unique and superior garden attributes. The Inventor crossed *Coreopsis* 'Sweet Dreams' (U.S. Plant Pat. No. 12,720) and *Coreopsis rosea* with *Coreopsis tinctoria* and another annual type species that are not commercialized and made six generations of crosses to produce interspecific hybrids to utilize in his breeding work. The new variety was developed with a goal of producing new cultivars of *Coreopsis* with unique flower colorations, short and bushy plant habits, and sterility to lengthen bloom periods.

The Inventor made a controlled cross in August 2006 in his test garden in Hubbardston, Mass. between an unnamed F6 generation seedling produced from crosses of *Coreopsis tinctoria* and *Coreopsis rosea* as the female parent and an unnamed F6 generation seedling produced from crosses of unnamed hybrid *Coreopsis* from his breeding program and

*Coreopsis rosea* as the male parent. 'Salsa' was selected in August 2007 as a single unique plant amongst the resulting seedlings.

Asexual reproduction of the new cultivar was first accomplished by stem cuttings in Kensington, Conn. in August of 2007 under the direction of the Inventor. The characteristics of this cultivar have been determined to be stable and are reproduced true to type in successive generations.

SUMMARY OF THE INVENTION

The following traits have been repeatedly observed and are determined to be the characteristics of the new cultivar. These attributes in combination distinguish 'Salsa' as unique from all *Coreopsis* cultivars and species known to the Inventor.

1. 'Salsa' exhibits composite inflorescences with ray florets that are gold in color with a large dark red eye zone.
2. 'Salsa' exhibits a bushy plant habit and is relatively short in height; reaching 12 to 18 inches (30 to 45 cm) in height.
3. 'Salsa' exhibits a vigorous growth habit.
4. 'Salsa' exhibits a floriferous and long blooming habit; blooming from June through August in Massachusetts.
5. 'Salsa' is relatively sterile and produces very few seeds if any.

The female parent differs from 'Salsa' in having a shorter plant height (reaching 8 to 12 inches in height), in having inflorescences with ray florets that are white in color with a small burgundy eye, and in producing an abundance of seed that shortens its bloom season to one month. The male parent differs from 'Salsa' in being taller in plant height (reaching 18 to 24 inches in height), in being less floriferous and in having inflorescences with ray florets that are solid gold in color. 'Salsa' can be most closely compared to cultivars from the same parentage, 'Cha Cha Cha' and 'Jive'. Both are similar to 'Salsa' in plant habit, plant height, and blooming habit. 'Cha Cha Cha' differs from 'Salsa' in having inflorescences with ray florets that are gold in color with a much smaller dark red eye zone. 'Jive' differs from 'Salsa' in having inflorescences with ray florets that are white in color with large eye zones that are dark burgundy-purple in color.

BRIEF DESCRIPTION OF THE DRAWING

The accompanying colored photographs illustrate the overall appearance and distinct characteristics of the new *Coreopsis*.

The photograph in FIG. 1 was taken in late summer of two five month-old plants of 'Salsa' as grown in a mixed container planting in New Hope, Minn. and illustrates the bushy plant habit and floriferous blooming habit of 'Salsa'.

Figure 1:
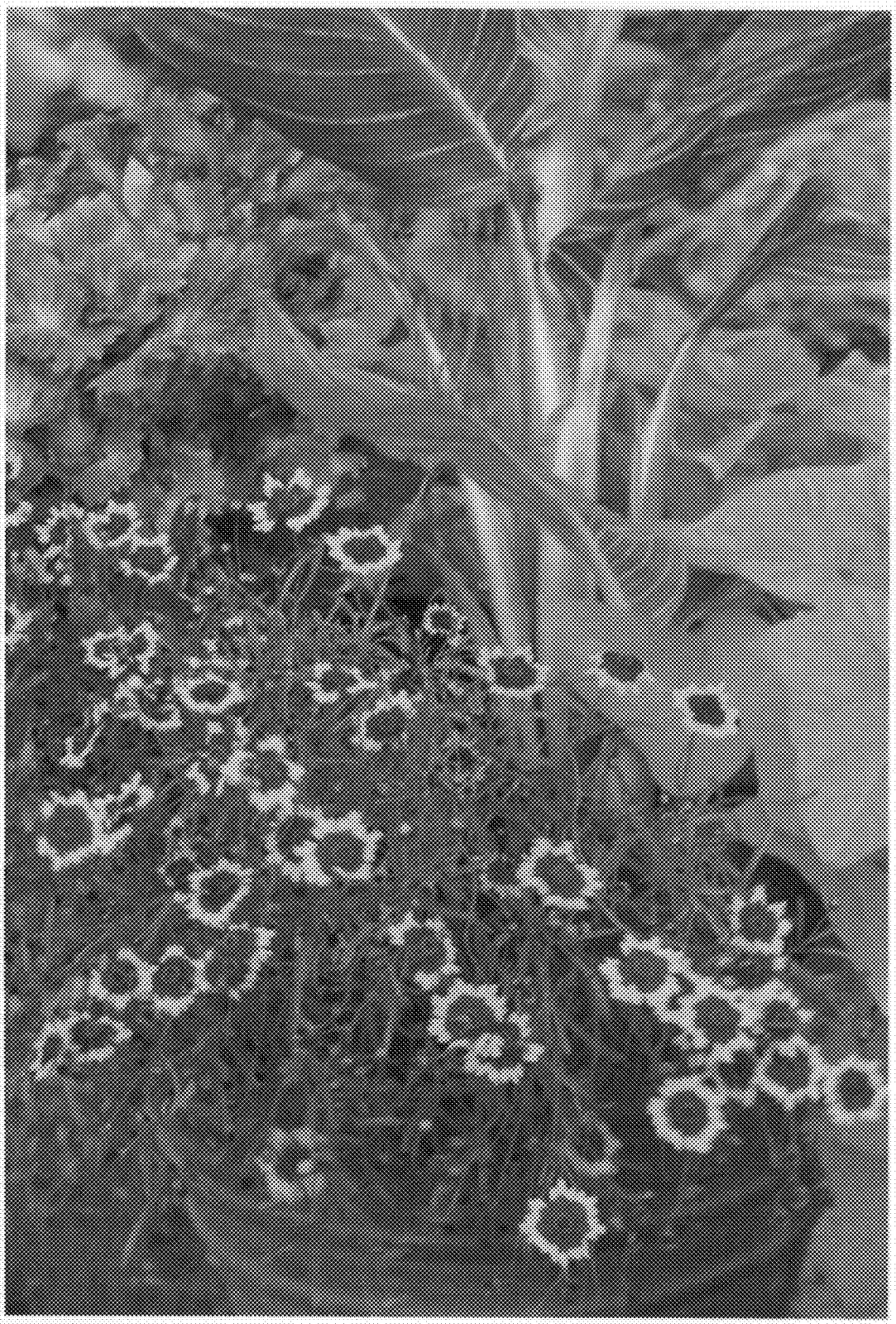
Figure 2:
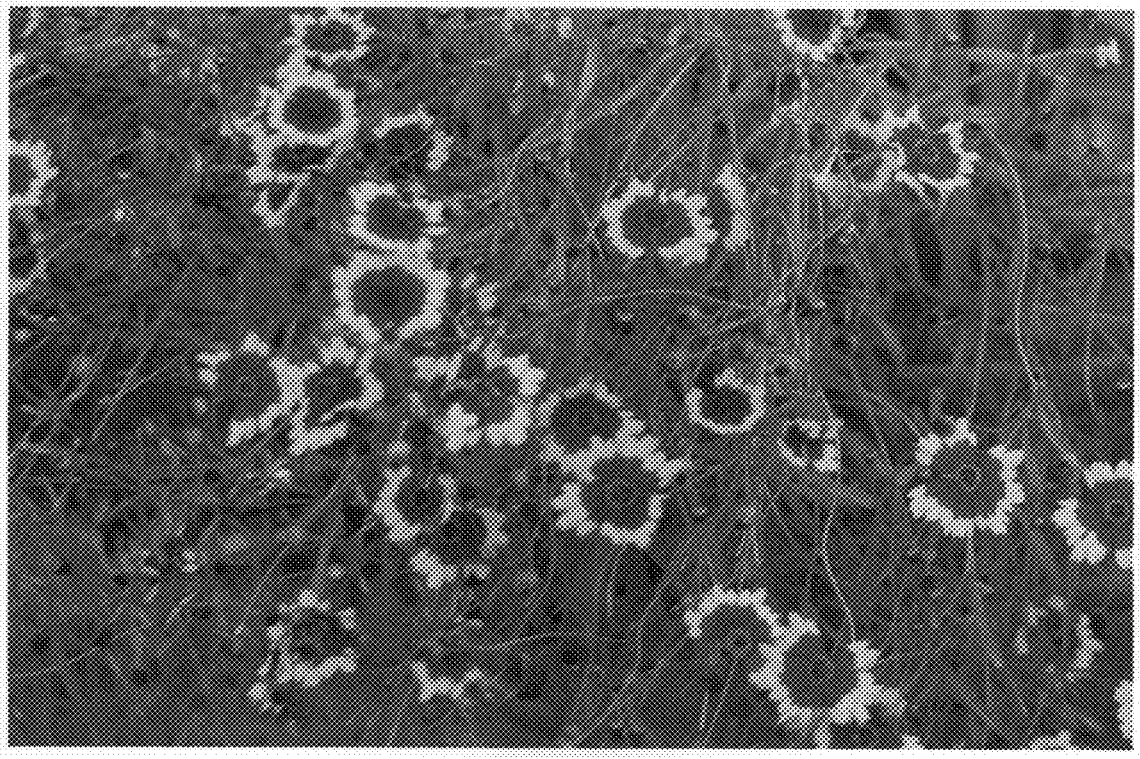

The photograph in FIG. 2 provides a close-up view of inflorescences of 'Salsa'.

The colors in the photograph may differ slightly from the color values cited in the detailed botanical description, which accurately describe the colors of the new *Coreopsis*.

DETAILED BOTANICAL DESCRIPTION

The following is a detailed description of the new cultivar as observed for three growing seasons in a trial garden in Hubbardston, Mass. with the detailed botanical data collected from five month-old plants of the new cultivar as grown in two-gallon containers in New Hope, Minn. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—Blooms from June through August in central Massachusetts.

*Plant habit.*—Herbaceous annual, well-branched to produce a bushy habit.

*Height and spread.*—Reaches 12 to 18 inches (30 to 45 cm) in height and 12 to 15 inches (30 to 38 cm in width) in 3 months from a rooted cutting.

*Cold hardiness.*—Has not been tested as it is grown as an annual.

*Diseases resistance.*—No particular resistance or susceptibility has been observed.

*Root description.*—Fibrous, fine and well-branched.

Growth and propagation:

*Propagation.*—Terminal stem cuttings.

*Growth rate.*—Vigorous.

Stem description:

*Shape.*—Oval, solid.

*Stem color.*—146B and lightly suffused 187C on mature stems.

*Stem size.*—Main stem averages 30 cm in length with laterals an average of 21 cm in length (excluding peduncles), an average of 2.5 mm in width.

*Stem surface.*—Very finely puberulent with some ridges when mature.

*Branching habit.*—An average of 5 basal branches with an average of 4 lateral branches, and 3 terminal flowering branches, branch internode length is variable but typically about 6 cm.

Foliage description:

*Leaf division.*—Simple.

*Leaf margins.*—Primarily tri-lobed.

*Leaf size.*—Up to 6 cm in length and 4.5 cm in width, when tri-lobed 4 cm in length and 6 mm in width and side lobes 3.3 cm in length and 5 mm in width.

*Leaf shape.*—Fan shaped overall when tri-lobed with lobes narrowly lanceolate to linear.

*Leaf base.*—Attenuate.

*Leaf apex.*—Acute.

*Leaf venation.*—Pinnate, not prominent, both surfaces 138B in color.

*Leaf attachment.*—Sessile.

*Leaf arrangement.*—Opposite.

*Leaf internode length.*—Average of 4.5 cm.

*Leaf quantity.*—An average of 15 per main stem.

*Leaf surface.*—Dull and very finely puberulent on upper surface and lower surface.

*Leaf color.*—Young and mature upper surface; 137A, young and mature lower surface; 137B.

Inflorescence description:

*Inflorescence type.*—Composite with ray florets surrounding disk florets in the center forming a radiant head, inflorescences are borne singular to group of 3 at terminal of lateral branches.

*Lastingness of inflorescence.*—About one week until senescence of ray florets, bracts and disk florets are persistent.

*Fragrance.*—None detected.

*Quantity of inflorescences.*—An average of 18 per main branch.

*Inflorescence size.*—Average 1 cm in depth and up to 3 cm in diameter with disk portion an average of 8 mm in diameter.

*Inflorescence buds.*—Average of 5 mm in depth and 6 mm in diameter, shape is spherical, color is a blend of 31A , 153D and 137B, with bracts 137B.

*Peduncle.*—Average of 6 cm in length and 1.5 mm in diameter, 146A in color, finely puberulent surface.

Involucral bracts:

*Bract number.*—Two rows of 8.

*Bract arrangement.*—Outer bracts are un-fused spreading and held nearly horizontal, inner bracts overlap and surround receptacle with a campanulate form with apical portion un-fused, spreading, and held close to ray florets.

*Bract size.*—Outer bracts about 2 mm in length and 1 mm in width, inner bracts about 6 mm in length and 2.5 mm in width with free portion an average of 3.5 mm in length and 2.5 mm in width.

*Bract color.*—Outer bracts 138A in both surfaces, inner bracts; fused portion 138A, un-fused portion is a blend of 138B and 35A with apex and margin 187A.

*Bract texture.*—Outer bract; puberulent, waxy, inner bracts glabrous and waxy.

*Bract apex.*—Outer bract; acute, inner bracts; acute.

*Bract base.*—Truncate.

*Bract shape.*—Outer bracts; lanceolate, inner bracts; free portion broadly ovate.

Ray florets (sterile):

*Number.*—8.

*Shape.*—Ovate, appearance of three longitudinal sections with center section longer.

*Size.*—Average of 1.4 cm in length and 1.2 cm in width.

*Apex.*—Emarginate.

*Base.*—Broadly cuneate.

*Margins.*—Entire on sides, divided into 3 lobes at apex.

*Aspect.*—Held nearly horizontal and slightly cupped upward, slightly wavy.

*Surface.*—Glabrous on both surfaces.

*Color.*—Upper surface opening and fully open; lower half 59A with upper half 17A, lower surface opening and fully open; 17C heavily suffused with 178A.

Disk florets (male and female):

*Shape.*—Tubular, corolla is fused, flared at apex.

*Size.*—About 3 mm in length and 0.7 mm in width.

*Color.*—In masse; 59A when opening and becoming primarily 34A when fully open and mature, corolla; base (tube) is 160A, flared portion is 160A and translucent.

*Receptacle.*—About 3 mm in diameter and 2 mm in depth, 145A in color.

Reproductive organs:

*Presence.*—Disk florets are perfect, ray florets are sterile.

*Gynoecium.*—1 Pistil, 2.5 mm in length, style is very fine and about 160A in color and translucent, bifid pilose stigma is 170A in color with branches about 0.7 mm in length and recurved, ovary is 1 mm in length, 0.5 mm in width, inferior, and 145D in color.

*Androcoecium.*—5 stamens, fused into tube surrounding style, 1.5 mm in length and 0.3 mm in width, about 200A in color, no pollen was observed.

*Fruit/seed.*—Relatively sterile and produces very few seeds if any.

It is claimed:

1. A new and distinct cultivar of *Coreopsis* plant named 'Salsa' as herein illustrated and described.

* * * * *